(12) United States Patent (10) Patent No.: US 8,163,510 B2
Shults et al. (45) Date of Patent: *Apr. 24, 2012

(54) QUANTITATIVE ZAP-70 ASSAY

(75) Inventors: Keith E. Shults, Nolensville, TN (US);
Angel L. Flye, Chapel Hill, NC (US);
Leigh Ann Hobbs, Brentwood, TN (US); David Miller, Brentwood, TN (US)

(73) Assignee: Esoterix, Inc., Brentwood, TN (US)

(*) Notice: Subject to any disclaimer, the term of this patent is extended or adjusted under 35 U.S.C. 154(b) by 0 days.

This patent is subject to a terminal disclaimer.

(21) Appl. No.: 12/838,906

(22) Filed: Jul. 19, 2010

(65) Prior Publication Data

US 2011/0020844 A1 Jan. 27, 2011

Related U.S. Application Data

(63) Continuation of application No. 11/251,271, filed on Oct. 14, 2005.

(51) Int. Cl.
*G01N 33/574* (2006.01)
*G01N 33/53* (2006.01)

(52) U.S. Cl. .......... 435/7.23; 435/7.1

(58) Field of Classification Search .......... None
See application file for complete search history.

(56) References Cited

U.S. PATENT DOCUMENTS

| 7,329,502 | B2 | 2/2008 | Staudt et al. |
| 7,759,076 | B2 | 7/2010 | Shults et al. |
| 2003/0203416 | A1 | 10/2003 | Staudt et al. |
| 2008/0227741 | A1 | 9/2008 | Staudt et al. |

OTHER PUBLICATIONS

Herishanu et al (Leukemia, 2005, 19: 1289-1291; Published online Apr. 21, 2005, IDS).*
Crespo et al (N Eng J Medicine, 2003, 348:1764-1775, IDS).*
Herishanu et al (Leukemia & Lymphoma, 2005, 46 (Suppl 1):S48, IDS).*
Admirand, J. et al., "Immunohistochemical detection of ZAP-70 in 341 cases of non-Hodgkin and Hodgkin lymphoma," 2004, Modern Pathology, 17:954-961.
Bosch, F. et al., "Clinical Implications of ZAP-70 Expression in Chronic Lymphocytic Leukemia," 2006, Clinical Cytometry, 70B:214-217.
Byrd, J. et al., "Chronic Lymphocytic Leukemia," 2004, Hematology, 1:163-183.
Chen, L. et al., "Expression of ZAP-70 is associated with increased B-cell receptor signaling in chronic lymphocytic leukemia," 2002, Blood, 100:4609-4614.
Crespo, M. et al., "ZAP-70 Expression as a Surrogate for Immunoglobulin-Variable-Region Mutations in Chronic Lymphocytic Leukemia," 2003, N. Engl. J. Med., 348:1764-1775.
Durig, J. et al., "ZAP-70 expression is a prognostic factor in chronic lymphocytic leukemia," 2003, Leukemia, 1-9.
Firestein, G., "The T cell cometh: interplay between adaptive immunity and cytokine networks in rheumatoid arthritis," 2004, J. Clinical Investigation, 114:471-474.
Herishanu, Y. et al., "Quantitative flow cytometry of ZAP-70 levels in CLL using molecules of equivalent soluble fluorochrome: B-CLL cell and T-Cell ZAP-70 levels correlate with disease progression," 2005, Leukemia & Lymphoma, 46:S48.
Herishanu, Y. et al., "T-cell ZAP-70 overexpression in chronic lymphocytic leukemia (CLL) correlates with CLL cell ZAP-70 levels, clinical stage and disease progression," 2005, Leukemia, 19:1289-1291.
Latour, S. and Veillette, A., 2001, "Proximal protein tyrosine kinases in immunoreceptor signaling," 2001, Current Opinion in Immunology, 13:299-306.
Letestu, R. et al., "Evaluation of ZAP-70 Expression by Flow Cytometry in Chronic Lymphocytic Leukemia: A Multicentric International Harmonization Process," 2006, Clinical Cytometry, 70B:309-314.
Mainou-Fowler, T. et al., "The Prognostic Value of CD38 Expression and its Quantification in B Cell Chronic Lymphocytic Leukemia (B-CLL)," 2004, Leukemia & Lymphoma, 45:455-462.
NIST Calibration Particles, 2008, Polysciences, Inc.
Orchard, J. et al., "ZAP-70 expression and prognosis in chronic lymphocytic leukaemia," 2004, Lancet, 363:105-111.
Otsu, M. et al., "Reconstruction of lymphoid development and function in ZAP-70-deficient mice following gene transfer into bone marrow cells," 2002, Blood, 100:1248-1256.
Rainbow Calibration Particles (8 peaks), 3.0-3.4 μm, Technical Data Sheet, Sphero.
Rassenti, L. et al., "ZAP-70 Compared with Immunoglobulin Heavy-Chain Gene Mutation Status as a Predictor of Disease Progression in Chronic Lymphocytic Leukemia," 2004, N. Engl. J. Med., 351:893-901.
Rosenwald, A. et al., "Relation of Gene Expression Phenotype to Immunoglobulin Mutation Genotype in B Cell Chronic Lymphocytic Leukemia," 2001, J. Experimental Medicine, 194:1639-1647.
Sakaguchi, N. et al., "Altered thymic T-cell selection due to a mutation of the ZAP-70 gene causes autoimmune arthritis in mice," 2003, Nature, 426:454-460.
Schwartz, A. et al., "Quantitating Fluorescence Intensity from Fluorophore : The Definition of MESF Assignment," 2002, J. Res. Natl. Inst. Stand. Technol., 107:83-91.
Shanafelt, T. et al., "Prognosis at diagnosis: integrating molecular biologic insights into clinical practice for patients with CLL," 2004, Blood, 103:1202-1210.
Shankey, T. et al., "An Optimized Whole Blood Method for Flow Cytometric Measurement of ZAP-70 Protein Expression in Chronic Lymphocytic Leukemia," 2006, Clinical Cytometry, 70B:259-269.
Shults, K. et al., "A Standardized ZAP-70 Assay—Lessons Learned in the Trenches," 2006, Clinical Cytometry, 70B:276-283.
Solberg, H. and Stamm, D., "Approved Recommendation on the Theory of Reference Values," 1991, Eur. J. Clin. Chem. Clin. Biochem., 29:531-535.
Stevenson, F. and Caligaris-Cappio, F. "Chronic lymphocytic leukemia: revelations from the B-cell receptor," 2004, Blood, 103:4389-4395.

(Continued)

*Primary Examiner* — Laura B Goddard
(74) *Attorney, Agent, or Firm* — Kilpatrick Townsend & Stockton LLP (57) ABSTRACT

An quantitative ZAP-70 assay is provided, with ZAP-70+ and ZAP-70− controls, normal human blood controls, an improved antibody with better signal to noise ratio, and using the median MEFL that is calibrated using a standard curve.

12 Claims, 7 Drawing Sheets

OTHER PUBLICATIONS

Tockman, M. et al., "Considerations in Bringing a Cancer Biomarker to Clinical Application," 1992, Cancer Research, 52:2711s-2718s.

van Oers, N. and Weiss, A., "The Syk/ZAP-70 protein tyrosine kinase connection to antigen receptor signalling processes," 1995, Seminars in Immunology, 7:227-236.

Wange, R., "TCR Signaling: Another Abl-Bodied Kinase Joins the Cascade," 2004, Current Biology, 14:R562-R564.

Wiestner, A. et al., "ZAP-70 expression identifies a chronic lymphocytic leukemia subtype with unmutated immunoglobulin genes, inferior clinical outcome, and distinct gene expression profile," 2003, Blood, 101:4944-4951.

Wong, W. and Leong, K., "Tyrosine kinase inhibitors: a new approach for asthma," 2004, Biochimica et Biophysics Acta, 1697:53-69.

* cited by examiner

Fig. 1: Standard Curve—Conversion of Mean Channels to MEFL

FIG. 2. Comparison of Fluorochrome Peformance

FIG. 5. MEFL Levels of T Cells in Normal Patients vs. CLL Patients

Fig. 7. Multiple Site Data

QUANTITATIVE ZAP-70 ASSAY

PRIOR RELATED APPLICATIONS

The present application is a continuation of U.S. patent application Ser. No. 11/251,271, filed Oct. 14, 2005, now issued as U.S. Pat. No. 7,759,076, the contents of which are incorporated by reference herein in its entirety.

FEDERALLY SPONSORED RESEARCH STATEMENT

Not applicable.

FIELD OF THE INVENTION

The invention relates to an improved ZAP-70 prognostic assay based on flow cytometry. The assay is improved by being made quantitative, rather than qualitative—that is rather than providing a simple yes/no answer for the ZAP-70 expression test, a numerical result for the level of ZAP-70 expression is provided. Improvements include the use of a standard curve of fluorescence per unit antibody; the use of a first control containing both ZAP-70$^+$ and ZAP70$^-$ cells, and the use of normal blood samples as assay controls, and finally, two cutoff values are provided, rather than single cutoff. The assay is thus made considerably more reliable than the prior art assays, and can be effectively used in predicting the prognosis of chronic lymphocytic leukemia.

BACKGROUND OF THE INVENTION

Chronic lymphocytic leukemia (CLL) is a malignancy of bone marrow cells (lymphocytes) that is found mostly in older people. It affects about 8,200 Americans each year, representing about 22-30% of all leukemia cases according to the National Cancer Institute. Many patients with CLL live for a long time without treatment and survive many years after diagnosis. Others, however, have disease that rapidly progresses and leads to death within a few years.

The clinical problem has been how to distinguish between these two groups of patients in order to treat each group appropriately. Since the late '90s it has been known that the presence or absence of somatic mutations in the immunoglobulin heavy chain variable (IgVH) regions of CLL cells provides a reliable distinguishing characteristic between these two patient populations. Patients whose CLL cells express un-mutated IgVH regions usually have early progression of their disease, whereas patients with mutated IgVH regions usually have later progression.

However, one major shortcoming of using IgVH mutations as a biomarker for CLL is that most clinical laboratories are not capable of detecting IgVH mutations. Even if readily available, the technology is expensive to implement and time consuming, making it impractical for widespread screening of all CLL patients. Thus, scientists have been searching for a reliable surrogate marker for IgVH mutation.

Rosenwald found such a marker. In 2001 his group reported that Zeta-associated protein of 70 kDa (ZAP-70), a cytoplasmic tyrosine kinase essential for T-cell-receptor signal transduction, is preferentially expressed in CLL B-cells whose immunoglobulin genes have not undergone somatic hypermutation, while a second CLL subtype with mutated immunoglobulin genes most often lacks ZAP-70 expression. Rosenwald (2001); US2003203416.

Patients with less ZAP-70 in their B-cells were more likely to have mutations, and lived anywhere from 15 to 34 years after their diagnosis, with an average survival of 24.4 years. On the other hand, CLL patients whose cells contained significant ZAP-70 were less likely to have mutations and lived from 7 to 11.5 years, with an average of 9.3 years. Recently, it was shown that ZAP-70 expression in T-cells correlates with B-CLL ZAP-70 and bears the same correlation with time to clinical progression of the disease (Herishanu 2005).

The use of ZAP-70 as a marker for IgVH mutation was initially very promising, however, subsequent studies have cast doubt on its prognostic value. Researchers have criticized the current ZAP-70 assays, as follows:

> However, for both CD38 and ZAP-70, subsequent studies have yielded controversial results with regard to their validity as a surrogate marker for VH and prognostic indicator. The facts that (1) divergent results have been obtained in different laboratories (CD38 and ZAP-70), (2) the expression level may change over time (CD38), (3) a careful separation of T-cells is necessary (ZAP-70), (4) different cut-off values to distinguish "positive" from "negative" cases were defined (CD38 and ZAP-70), and (5) approximately 10%-30% of cases show discordant status for CD38 or ZAP-70 as compared to VH in all series described, indicate that these markers may not be as reliable as initially thought for routine diagnostics.
>
> Byrd (2004) (cites omitted) (emphasis added).

The National Cancer Institute has also noted that the test is not standardized: "This test, which is commercially available, but has not undergone national standardization, has been proposed as a surrogate for the mutational status." Our own lab has noted that ZAP-70 is present only in low copy number against a large background of noise, and these facts have hindered the realization of the true prognostic value of the ZAP-70 assay. Thus, it is apparent that the use of the ZAP-70 assay as a prognostic tool needs considerable improvement. What is needed in the art is a standardized assay with increased reliability, sensitivity and greater quantitative precision.

SUMMARY OF THE INVENTION

The following abbreviations are used in herein:

TABLE 1

Abbreviations

| Abbreviation | Expansion |
|---|---|
| ABC | Antibody Binding Capacity - The ABC is the number of monoclonal antibodies a sample will bind, and correlates to the number of antigens expressed on the cell surface. |
| Eff. F/P | The effective number of fluorochrome molecules conjugated per each antibody molecule determined by measured fluorescence intensity of antibody capture microspheres measured on a flow cytometer calibrated in units of fluorochrome specific MESF |

TABLE 1-continued

Abbreviations

| Abbreviation | Expansion |
|---|---|
| F/P | Number of fluorochrome molecules conjugated per each antibody molecule determined by absorbance on a spectrophotometer. |
| FCS | Fetal Calf Serum |
| FSC | Forward angle light scatter |
| mAb | Monoclonal antibody |
| MESF | Molecules of Equivalent Soluble Fluorochrome. Corrects for changes in extinction coefficient, quenching, and small spectra shifts. Using the appropriate calibration controls, MESF and ABC can be calculated directly by the software that controls the cytometer. See also Molecules of Equivalent Soluble Fluorochrome or MEFL, which is used interchangeably herein. |
| MFI | Mean Fluorescence Intensity |
| pAb | polyclonal antibody |
| PB | Peripheral blood |
| PBS | phosphate buffered saline (200 mg/l KCl; 200 mg/l KH2PO4; 8 g/l NaCl; 2.16 g/l Na2HPO4•7H2O, pH 7.4) |
| PermiFlow Working Solution | A 1:1 mixture of PermiFlow and Sigma water RNAse DNAse free |

"ZAP-70$^+$" or "ZAP-70 positive" cells are defined as cells having a significant and known level of ZAP-70 expression. "ZAP-70$^-$" or "ZAP-70 negative" cells have a much lower level of ZAP-70, but need not be completely devoid of ZAP-70 expression.

The routine, clinical determination of ZAP-70 expression in CLL has proved problematic in many laboratories. Poor precision, caused by the low copy number and a high level of non-specific normal or patient T-cells to define positivity. Instead, the invention binding, is a significant issue in connection with the assay. Accordingly, we have developed a quantitative assay that is standardized and provides better results.

Prominent in the literature (Crespo, 2003, Rassenti 2004) is the use of the tail of the distribution of ZAP-70 in normal or patient T-cells to define positivity. Instead, the invention uses a bead standard curve to convert MFI to MEFL using the medians of the distributions. The median is not dependent on the shape of the distribution and so has better precision. In this way we have shown that the prior art approaches contribute significantly to poor precision. We have also developed a Winlist protocol that helps to standardize the data analysis.

Extensive quality control measures are also necessary to assay precision. In addition to a daily normal peripheral blood control, the invention uses a cultured cell line system containing cells with known ZAP-70 levels. An on-going review of patient data for the relative number with a negative result is also useful. It is emphasized that meticulous laboratory technique, including the strict standardization of pipetting, incubation, and washing are of paramount importance to obtaining a reproducible assay.

In a preferred embodiment, the invention employs an Alexa Fluor® 647 conjugated anti-ZAP-70 antibody, rather than the more commonly used PE reagent, because of the better signal-to-noise ratio. In a further preferred embodiment, the patients samples are fresh blood, because blood storage decreases apparent ZAP-70 levels (Letestu 2005). Aged samples should be corrected for age-dependant reduction in ZAP-70 levels.

We analyzed 375 patients using the NCCLS (CLSI) rank-order, non-parametric approach to reference ranges to assign a cutoff for "negative." This cutoff was constructed at the 55th percentile of the patients studied. The next 15% of the rank-order were designated as "intermediate." The 35% with the highest values are, then, considered to be positive. The use of the two-cutoff rather than a single cutoff further improves the reliability of the assay.

Generally speaking the invention is a quantitative ZAP-70 assay described as follows: stain a first control cell population with an anti-ZAP-70 antibody, an anti-T-cell antibody and an anti-B-cell antibody, wherein said first control cell population comprises mixture of ZAP-70$^+$ T-cells and ZAP-70$^-$ B-cells. In preferred embodiments, the first control cell population can be a mixture of Jurkat (a T-cell line) and Ramos cells (a B-cell line). In another preferred embodiment, a second control cell population comprising normal human blood can also be used. Measure anti-ZAP-70 antibody in the B-cells and T-cells by converting mean fluorescent intensity (MFI) of anti-ZAP-70 antibody to molecules of equivalent fluorochrome (MEFL) using a standard curve, and using the median of the population as the ZAP-70 value. Confirm that the amount of ZAP-70 in the first control cell population is within pre-established normal parameters, and if so, repeat on a patient sample, wherein if the level of ZAP-70 in the patient B-cells is in the top 30% indicates that the patient has progressive chronic lymphocytic leukemia (CLL), and if the level of ZAP-70 in the patient B-cells is in the lower 55% indicates that the patent has indolent CLL. In another embodiment, the level of ZAP-70 in T-cells can also be used, since T-cell ZAP-70 also correlates with time to progression of disease. An Alexa Fluor® 647 stain is particularly preferred. The T-cell antibody can be anti-CD5 antibody, and the anti-B-cell antibody can be anti-CD19 antibody, but many of the T- and B-cell antibodies are known and available.

Several anti-ZAP-70 antibodies are available, some of which are already conjugated to fluorescent probes. Those antibodies that are not conjugated can easily be conjugated with an appropriate dye using one of the many available conjugation kits. Commercial suppliers will also provide custom antibodies on demand. Exemplary antibodies include the following:

TABLE 2

Anti-ZAP-70 antibodies

| Vendor | Products |
|---|---|
| BD Biosciences Pharmingen ™ | #612588 Mouse Anti-ZAP-70 Kinase mAb, FITC Conjugated, Clone 29<br>Mouse Anti-ZAP-70 Kinase mAb, Unconjugated, Clone 24a<br>#612719 Mouse Anti-ZAP-70 Kinase Monoclonal Antibody, Unconjugated, Clone 24a<br>#612589 Mouse Anti-ZAP-70 Kinase Monoclonal Antibody, FITC Conjugated, Clone 29<br>#612718 Mouse Anti-ZAP-70 mAb, Unconjugated, Clone 29<br>#557818 Mouse Anti-Zap70 (Y319)/Syk (Y352) mAb, Alexa Fluor ® 488 Conjugated<br>#557817 Mouse Anti-Zap70 (Y319)/Syk (Y352) Mab, Alexa Fluor ® 647 Conjugated<br>#557881 Mouse Anti-Zap70 (Y319)/Syk (Y352) mAb, Phycoerythrin Conjugated |
| Biocare Medical ™ | #CM259A Mouse Anti-ZAP-70 Research Use Only mAb, Unconjugated |
| BioLegend ™ | #313403 Mouse Anti-ZAP-70 mAb, R-Phycoerythrin Conjugated, Clone 1E7.2<br># 313401 Mouse Anti-ZAP-70 mAb, Unconjugated, Clone 1E7.2 |
| CalTag Lab.™ | #MHZAP7000 Purified anti-human mouse ZAP-70<br>#MHZAP7020 Alexa Fluor 488 anti-human mouse ZAP-70<br>#MHZAP7004 R-PE anti-human mouse ZAP-70<br>#MHZAP7018 Pe-Cy5.5 anti-human mouse ZAP-70 |
| Cell Signaling Technology ™ | #2701S Anti-Zap-70, phospho (Tyr319)/Syk, phospho (Tyr352) Antibody, Unconjugated<br>#2704S Anti-Zap-70, phospho (Tyr493) Antibody, Unconjugated<br>#2704L Anti-Zap-70, phospho (Tyr493) Antibody, Unconjugated<br>#2707 Rabbit Anti-Zap-70 mAb, Alexa Fluor ™ 647 Conjugated, Clone 136F12<br>#2705 Rabbit Anti-Zap-70 mAb, Unconjugated, Clone 99F2 |
| Chemicon ™ | #AB1377 Anti-ZAP-70 (70 kDa zeta-associated protein) pAb, Unconjugated |
| Diagnostic BioSystems ™ | #Mob 431 Anti-ZAP-70 mAb, Unconjugated, Clone 2F3.2 |
| eBioscience ™ | #14-6695 Affinity Purified anti-mouse/human ZAP-70 (ZAP70)<br>#13-6695 Biotin anti-mouse/human ZAP-70 (ZAP70)<br>#11-6695 FITC anti-mouse/human ZAP-70 (ZAP70)<br>#12-6695 PE anti-mouse/human ZAP-70 (ZAP70)<br>#35-6695 Phycoerythrin-Cy5.5 (PE-Cy5.5) anti-mouse/human ZAP-70 (ZAP70) |
| GeneTex ™ | #GTX73804 ZAP-70 Mouse mAb<br>#GTX74255 ZAP-70 Rabbit pAb<br>#GTX12868 ZAP70 (phospho Y292) Rabbit pAb<br>#GTX12869 ZAP70 (phospho Y315 + Y319) Rabbit pAb<br>#GTX13957 ZAP70 Rabbit pAb<br>#GTX18384 ZAP70 Mouse mAb<br>#GTX18371 ZAP70 Mouse mAb<br>#GTX14827 ZAP70 Mouse mAb |
| Novus Biologicals ™ | #ab14827 Mouse Anti-ZAP70 mAb, Unconjugated, Clone 2F3.2<br>#ab13957 Rabbit Anti-ZAP70 Pab, Unconjugated<br>#ab12868 Rabbit Anti-ZAP70, phospho (Tyr292) Pab, Unconjugated #ab12869 Rabbit Anti-ZAP70, phospho (Tyr315/Tyr319) Pab, Unconjugated |
| OriGene ™ | #TA201071 Zap-70 (99F2) Rabbit mAb |
| Serotec Inc | #AHP470 Rabbit Anti-Human ZAP-70 Pab, Unconjugated |
| Spring Bioscience ™ | #E4634 Rabbit Anti-ZAP-70 Pab, Unconjugated |
| United States Biological ™ | #Z0300 Anti-Human ZAP 70 mAb, Unconjugated, Clone 0.T.155 |
| Upstate ™ | #06-271 Anti-ZAP-70<br>#05-776 Anti-ZAP-70, clone 1E7.2<br>#16-211 Anti-ZAP-70, clone 2F3.2, biotin conjugate, human<br>#16-210 Anti-ZAP-70, clone 2F3.2, FITC conjugate, human<br>#05-253 Anti-ZAP-70, clone 2F3.2, human<br>#05-253MG Anti-ZAP-70, clone 2F3.2, human<br>#16-214 Anti-ZAP-70, clone 2F3.2, (TRITC) Rhodamine conjugate, human |
| Zymed | Anti-ZAP-70 mAb, Unconjugated, Clone ZAP-70-6F7 |
| Tebu-Bio ™ | #021MHZAP7004 Anti ZAP-70 Human PE<br>#021MHZAP7020 Anti ZAP-70 Human Alexa 488 |

The fluorescent labels should be chosen with the operating characteristics of the cytometer in mind such that there is sufficient separation of signal so as to allow the cytometer to distinguish between the two or more signals. Many such labels are known in the art, including fluorescent isothiocyanate (FITC, aka fluorescein), Phycoerythrin (PE); Cy5PE; Cy7PE; Texas Red (TR); Allophycocyanin (APC); Cy5; Cy7APC; Cascade Blue; and the like. However, preferred labels are the Alexa Fluor® labels available from Invitrogen™, CalTag™, BD Biosciences™, etc., including Alexa Fluor® 350, 405, 430, 488, 500, 514, 532, 546, 555, 568, 594, 610, 633, 635, 647, 660, 680, 700 and 750 dyes. Particularly preferred is Alexa Fluor® 647.

In order to detect an intracellular target such as ZAP-70, cells must be fixed and permeabilized to allow the antibody to penetrate the cell and bind the antigen, while retaining sufficient cell morphology to allow cell separation. Thus, cells are permeabilized with agents such as 0.05% Triton X-100 in PBS, stained with antibody and then fixed. For example, PERMEAFIX™ or PERMIFLOW™ at mild denaturation or room temperatures preserves cell morphology and thus allows subsequent analysis by flow cytometry. Such methods are described in more detail in co-pending application 60/512,834 filed Oct. 20, 2003.

"Fixatives" are defined herein as fixatives that allow both cell fixation and permeation, while retaining cell surface morphology and DNA and RNA content, sufficient to allow separation of cells based on light scatter, surface epitopes and/or nucleic acid content. An acceptable fixative contains 0.75-0.85% formaldehyde, 25-30 mM DNBS, 6.8-7% DMSO and 0.08-0.1% Tween 20 detergent. A preferred fixative is PER-MIFLOW™.

BRIEF DESCRIPTION OF THE DRAWINGS

FIG. 5. MEFL Levels of T-cells in Normal Subjects vs. CLL Patients. FIGS. 4 and 5 are the same data represented in different ways; FIG. 4 is a FACS scatter plot, and FIG. 5 is the calculated MEFL for the various cell populations ($19^{th}$ Annual CCS meeting, Abs#12.p. 16, 2004). The Rassenti (2004) and Crespo (2003) papers use T-cell levels for ZAP-70 to set the threshold level for positivity in the CLL cells. As this data shows, the prior art assays lack precision because their one-point "standard" is a moving target.

DESCRIPTION OF EMBODIMENTS OF THE INVENTION

The present invention is exemplified with respect to CLL. However, it can be used for any disease for which ZAP-70 is a marker, including for example, severe combined immunodeficiency (SCID) (Otsu 2002), arthritis (Sakaguchi 2003), or other types of lymphoma (Admirand 2004).

The following examples describe the invention as practiced in additional detail, but should not be construed as limiting.

EXAMPLE 1

Materials

The sample can be any bone marrow or peripheral blood sample that is received in ACD, Sodium Heparin, or EDTA. In a preferred embodiment the sample is a fresh heparin sample. In addition to standard laboratory equipment, the following was used herein:

TABLE 3

| Equipment and reagents |
|---|
| Cytometer with filters for FITC, PE, Alexa fluor ® 647, and Alexa fluor ® 700. |
| anti-ZAP-70 Alexa fluor ® 647 (Cell Signaling Technology #2705) |
| Buffer QC (1.0 M NaCl, 50 mM MOPS pH 7.0, 15% isopropanol (v/v)) |
| Microsoft ™ Excel 2000 ™ |
| Newborn Calf Serum |
| PBS + 2% NCS |
| PermiFlow (Invirion ™ Corp. # 55001, Reagent #1) |
| PermiFlow Working Solution (1:1 mixture of PermiFlow ™ and Sigma ™ water RNAse/DNAse free) |
| Rainbow calibration particles (Spherotech, ™ Inc., Cat. #RCP-30-5A) |
| RPMI (Invitrogen ™ #11875119) |
| Surface Antibody Cocktail containing anti-CD5-FITC and anti-CD19-PE |
| Water (Sigma ™ #W4502) |
| WinList ™ Version 5.0 (Verity Software House ™) |

TABLE 4

| Antibodies | | |
|---|---|---|
| Cell Type | Antibody | Source |
| T-cells | anti-CD5-FITC | Immunotech IM#0468 |
| B-cells | anti-CD19-PE | Immunotech IM#1285 |
| T-, B-, and NK-cells | anti-ZAP-70-Alexa fluor ® 647 | Cell Sig. Tech. Cat # 2707 |
| T-, B-, and NK-cells | anti-ZAP-70-PE | Caltag ™ Catalog #MHZAP7004 |

EXAMPLE 2

Sample Preparation

About one million WBC cells/ml are needed for each patient sample. The antibodies employed are shown in Table 4, above.

Deliver 100 µl of adjusted blood sample to a 12×75 mm tube. Add titered amounts of Surface Antibody Cocktail or if cocktail is unavailable, use titered amounts of anti-CD5 FITC and anti-CD19 PE antibodies to prepare a "hand-made" cocktail. Vortex to mix. Allow to incubate in the dark for 20 minutes.

Wash tubes in 4 ml of PBS+2% NCS. Spin at 1300 rpm for 5 minutes, decant, and blot. Add 4 ml of prepared PermiFlow Working Solution to each tube and pipet up and down until there is no RBC pellet adhered to bottom of tube. Incubate at RT for 1 hour or at 4° C. overnight if test is to be completed the next working day.

Spin tubes to a pellet, decant, and add 4 ml of PBS+2% NCS, mix well with pipet. Spin to a pellet and repeat. If there is still a large amount of residual lysed red cell debris in the bottom of tube as indicated by a solid red pellet, repeat wash until residual lysed red cell debris is removed.

Add saturating, titered amounts of the anti-ZAP-70 Alexa 647 to each tube. Vortex to mix and incubate at RT for 1 hour. Wash twice in PBS+2% NCS. Re-suspend cells in 750 ul PBS+2% NCS.

Prepare Rainbow™ beads by adding 1 drop of vortexed Rainbow Bead suspension to 1 ml of Buffer QC. Collect Rainbow Bead data.

EXAMPLE 3

Flow Cytometry

We used the BECKMAN COULTER™ FC500 or BECTON DICKINSON™ FACS CALIBUR FLOW cytometer herein, but any properly quality controlled flow cytometer that satisfies established windows of analysis can be used, provided the laser excitation lines and filter configurations are correct for the excitation and detection of all fluorescence labels used in the assay. In general, we collect 50,000 ungated events. Data was analyzed in WinList (VERITY SOFTWARE™) and Excel (MICROSOFT™) or equivalent Exemplary results are shown in FIG. 1 through 6.

EXAMPLE 4

Antibody Optimization

Figure 1:
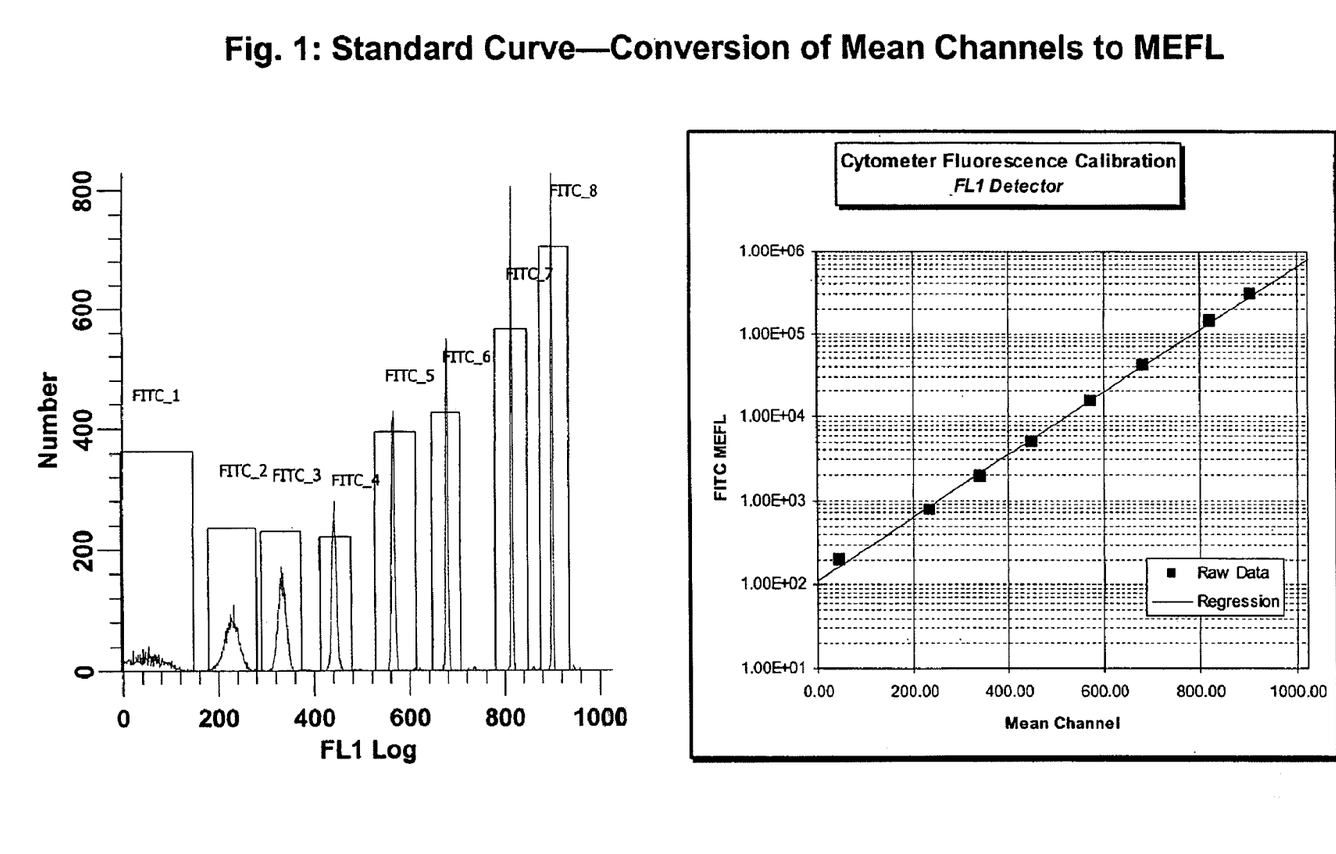
FIG. 1. Standard Curve—Conversion of Mean Channels to MEFL. Using the same standardized cytometry set-up in which patients are analyzed, a eight peak fluorescent standard is used to convert known equivalent fluorescent levels to linear mean channels (only six points shown in the graph). The derived slope and intercept are used to convert the MFI to MEFL.
Figure 2:
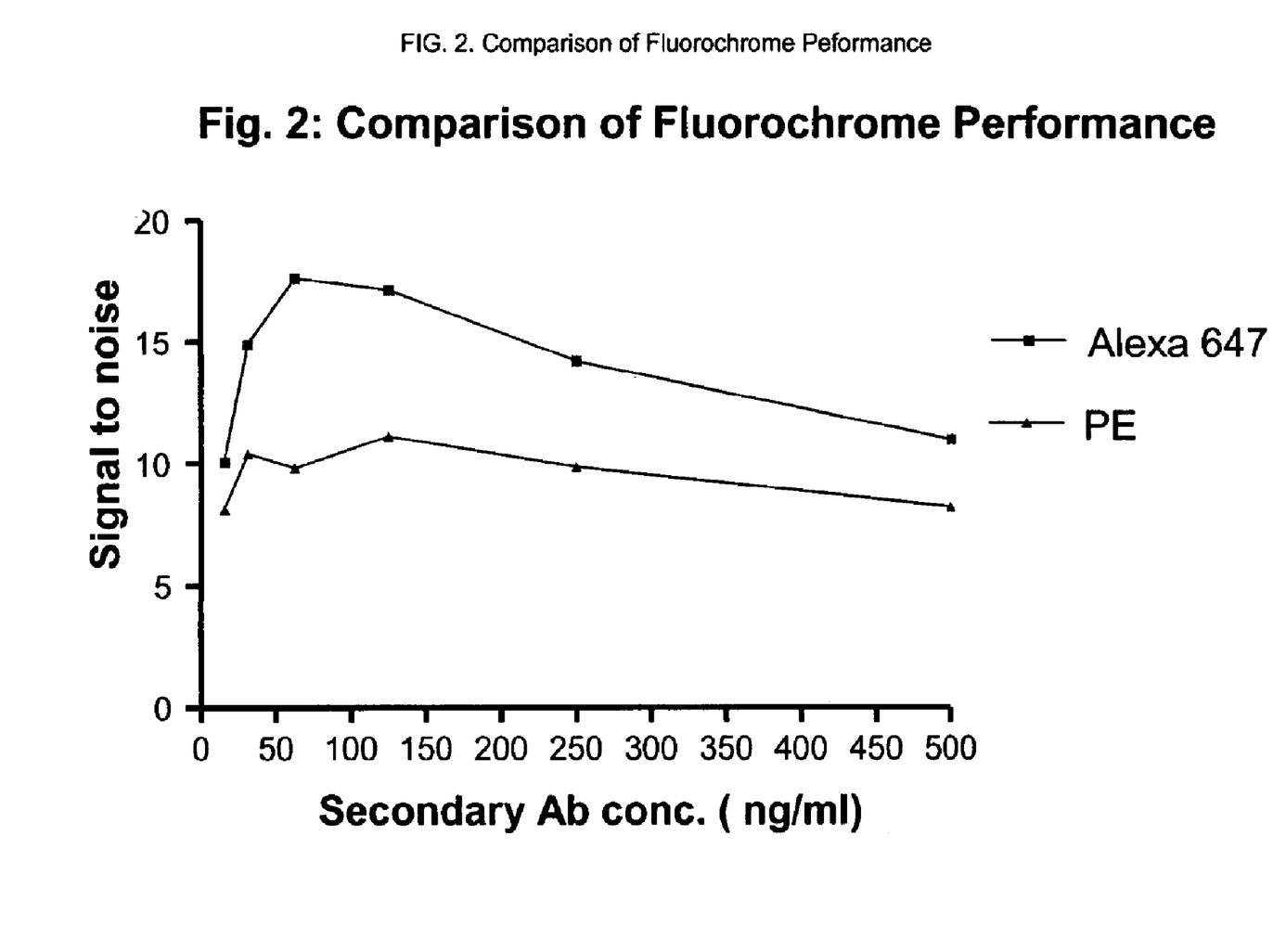
FIG. 2. Comparison of Fluorochrome Performance. Signal to noise ratio is plotted against antibody concentration for both Alexa Fluor® 647 and PE labeled antibodies. Alexa Fluor® 647 provides significantly improved signal to noise ratio, especially at lower concentrations. Cells were stained with the same primary antibody to SMAD-2 developed with secondary antibody conjugated to either Alexa 647 or PE and at the various concentrations.

One of the difficulties with the current assay is the ZAP-70 is expressed at only low levels and the signal to noise ratio with existing antibodies is poor. Thus, to fully optimize the assay, we also studied the fluorescent behavior of multiple fluorochromes. We assessed the performance of different fluorochromes at identical antibody concentrations. The graph in FIG. 2 depicts a typical finding comparing the SMAD-2 primary antibody developed with secondary antibodies conjugated to either PE or Alexa Fluor® 647 using the same flow cytometer. The graph teaches us three things: 1) In ranges of 0.5-2 µg, Alexa Fluor® 647 exhibits better signal to noise performance, and 2) there is a point where more antibody is not better, and 3) excess Alexa fluors are more easily removed from the cell in comparison to PE.

Figure 3:
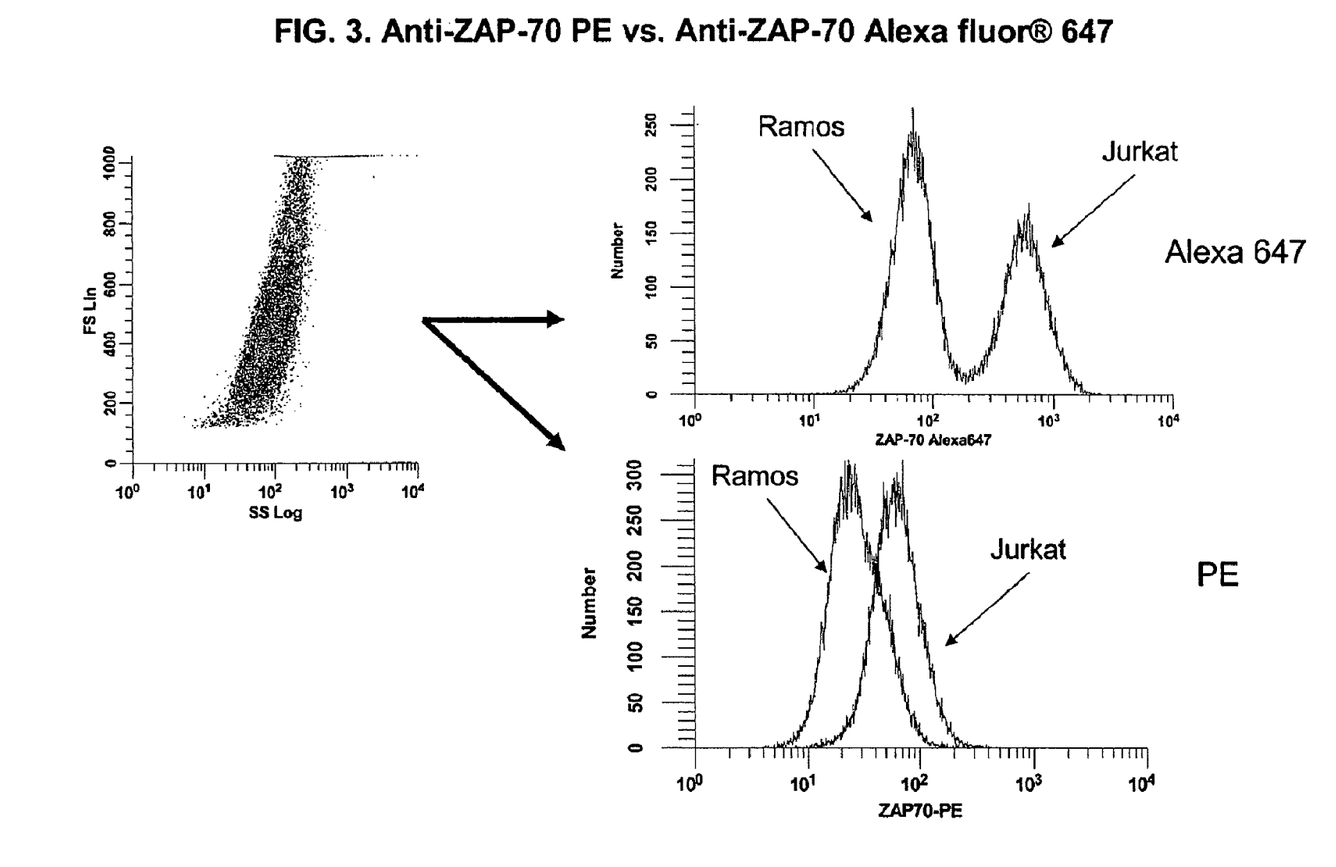
FIG. 3. Anti-ZAP-70 PE vs. Anti-ZAP-70 Alexa Fluor® 647. Separation of control cell populations—the ZAP-70 negative Ramos cell line and the ZAP-70 positive Jurkat cell line—is greatly improved with the Alexa Fluor® 647 label. This figure also illustrates the usefulness of these cell lines as positive and negative controls. This figure is predicted from the data presented in FIG. 2 and holds true in the detection of ZAP-70.
Figure 4:
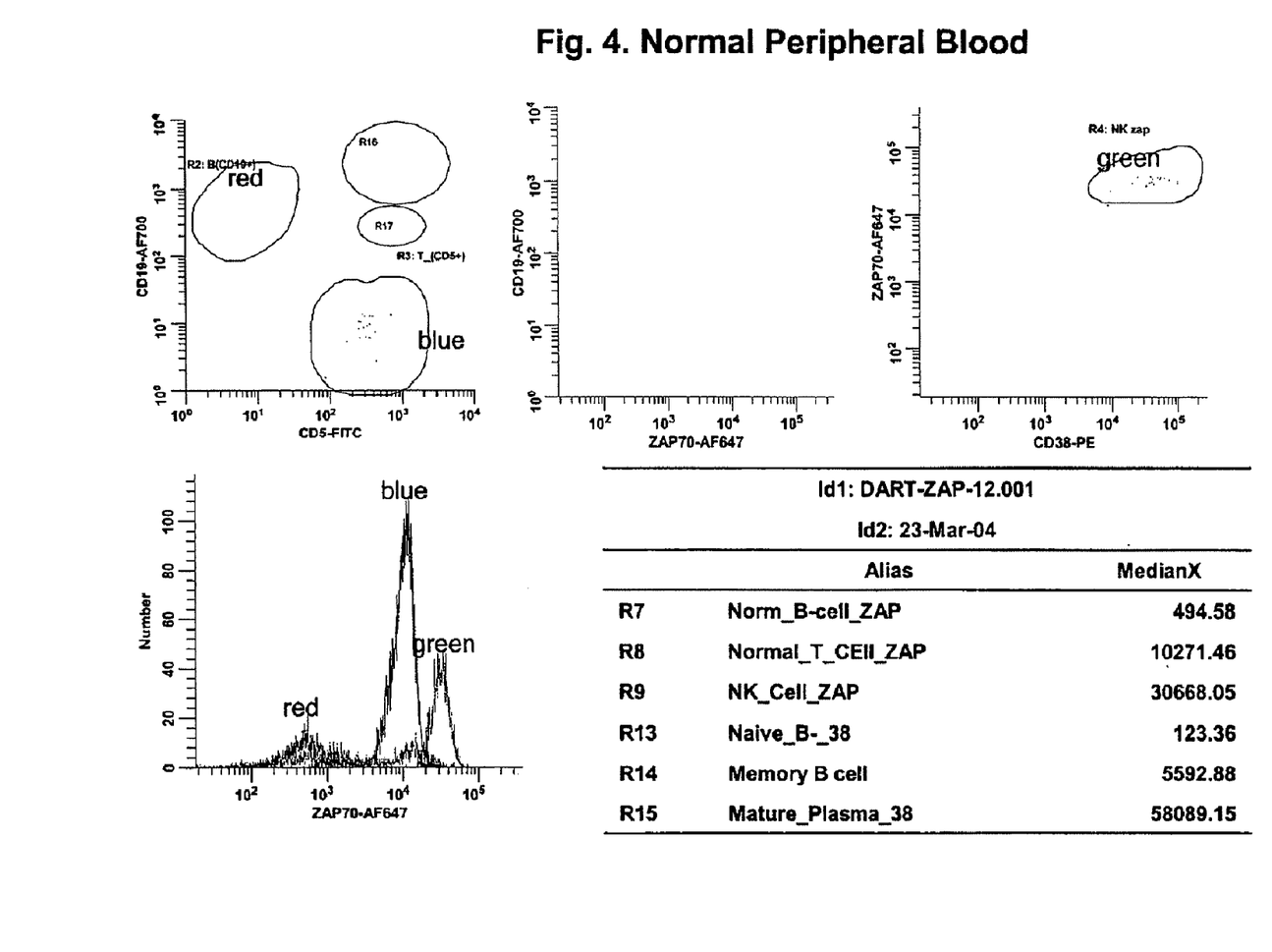
FIG. 4. Normal Peripheral Blood. The cells in blue represent T cells, the cells in red represent B cells and the cells labeled green are NK cells. The data has been converted to MEFL as evidenced by the median X values in the box. The single parameter histogram in the lower left demonstrates the ability to independently measure ZAP 70 levels in the various subsets.
Figure 5:
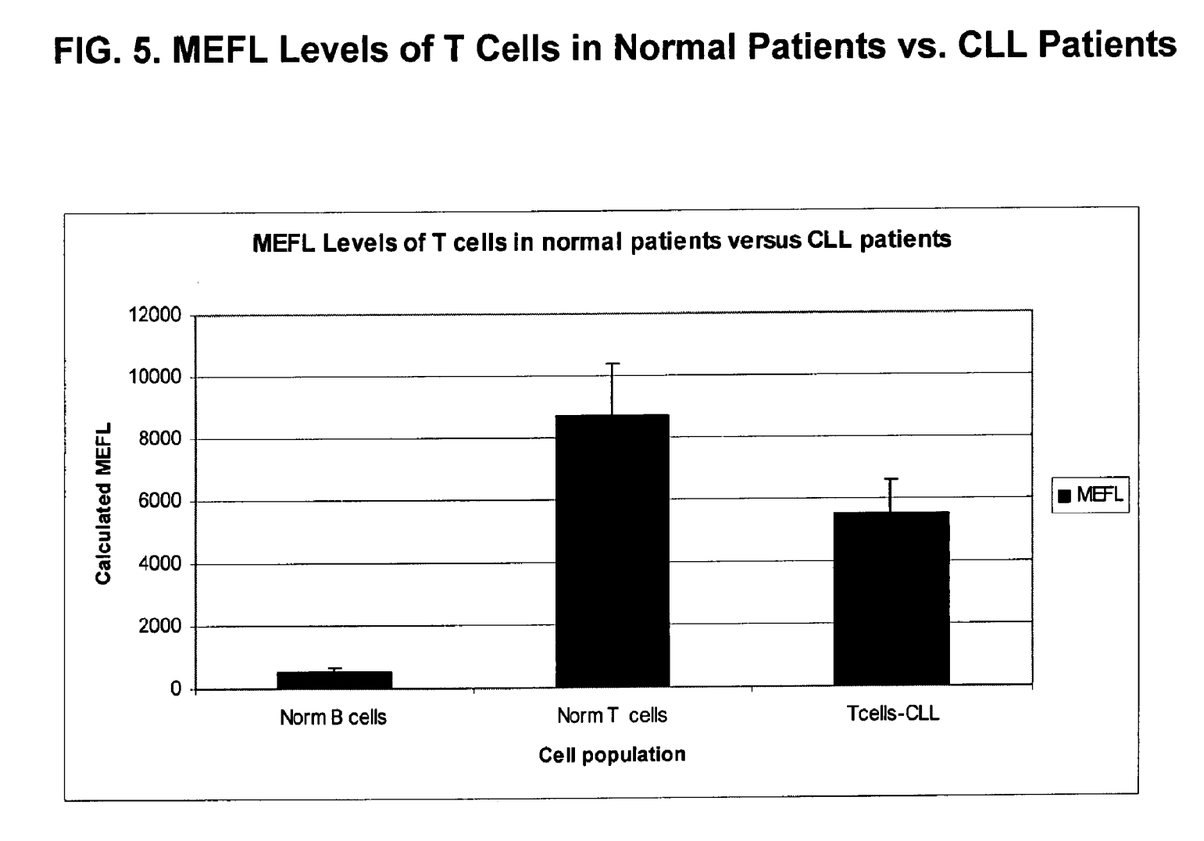
Figures 6, 6A:
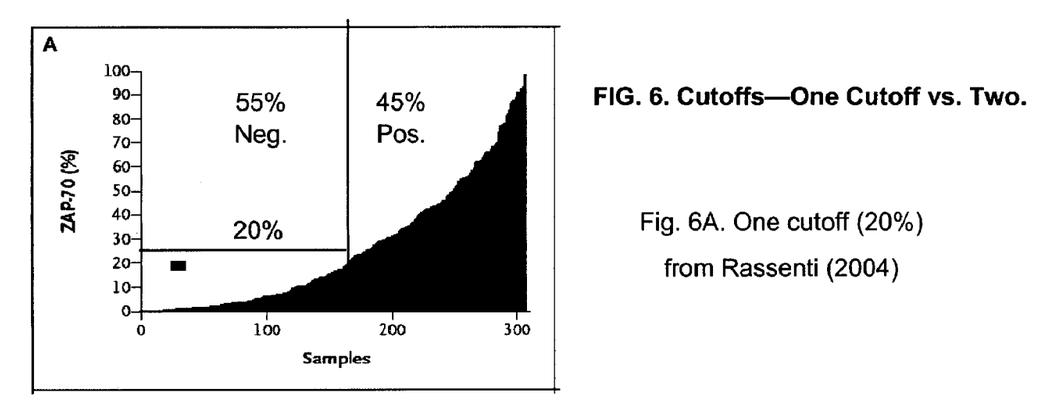
FIG. 6. Cutoffs—One Cutoff vs. Two. The prior used a single cutoff value to assign patients as ZAP-70 positive or negative (FIG. 6a). However, subsequent research has shown that this is too simplistic and a two cutoff assay is proposed in FIG. 6b. Here, patients with high ZAP-70 levels (greater than 2,100 MEFL) are positive, low ZAP-70 (less than 1350 MEFL) are negative, but those between 1,350 and 2,100 MEFL ZAP-70 are indeterminate.
Figure 6B:
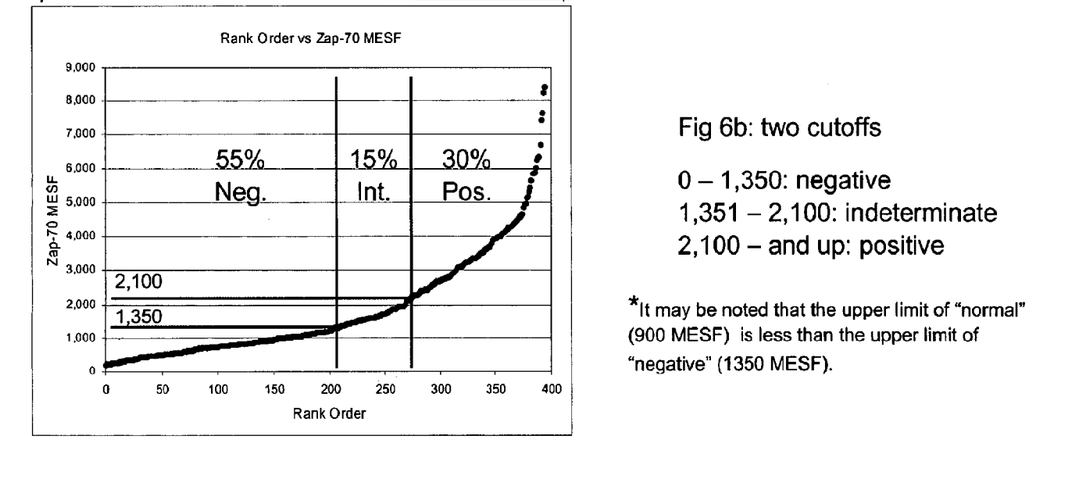

We then tested these labels in a real cell separation experiment using our Ramos/Jurkat controls (described in more detail below). We compared the anti-ZAP-70 rabbit monoclonal clone 136F12 conjugated with Alexa Fluor® 647 to a commercially available anti-ZAP-70 conjugated with PE. FIG. 3 shows greatly improved signal separation of the Alexa Fluor® based label, and it was chosen for all future experiments.

We also optimized the level of each antibody. Antibody titration data was plotted to show 1) staining intensity versus antibody staining concentration, 2) percent positive staining versus concentration and 3) the signal to noise ratio versus concentration (data not shown). These plots aided in the identification of the optimal staining concentration of each antibody, indicated whether saturation staining was possible for each antibody. The minimal antibody that provided saturation staining was chosen for future experiments.

EXAMPLE 5

Assay Design

An improved ZAP-70 assay should meet one of more of these basic criteria: 1) the assay should be adaptable to peripheral blood, bone marrow, and cell line systems; 2) the assay should be multiparametric with a preferred minimum of 6 parameters (FSC,SSC,FITC/PE/Alexa647/Alexa700) combining surface/cytoplasmic staining; 3) The assay should collect data uncompensated to remove hardware bias (technologists who enter hardware values incorrectly can bias quantitative values versus off-line software compensation); 4) The assay should convert fluorescence parameters to MEFL and quantitate all fluorescence parameters; and 5) the assay should measure each cell population independently. Therefore, we designed a ZAP-70 assay to meet these needs.

Our ZAP-70 assay requires the mean fluorescence intensity (MFI) to be converted to molecules of equivalent fluorochrome (MEFL). MEFL provides a more precise indicator of ZAP-70 expression because it equates the median intensity of the populations relative to a known, stable standard. This is done using an 8 peak fluorescent standard to correlate known equivalent fluorescent levels to linear mean channels. The slope and intercept are derived by linear regression and used to convert the median intensity to MEFL.

To further improve our assay we have added two types of quantitative controls. One of our controls is a mixture of equal numbers of Jurkat and Ramos cells. Jurkat cells express significant ZAP-70, while Ramos cells express much less ZAP-70. Thus, this mixture of cells provides useful positive and negative controls for the assay (see e.g., FIG. 3). This material controls for cell fixation, permeation, antibody staining and ZAP-70 expression levels across different laboratories and equipment. It also accounts for proper removal of excess antibody because elevated levels in the Ramos cells indicate poor lab technique.

We also employ a second kind of semi-quantitative control, using blood from normal subjects. About 100 µl of blood is stained from a normal subject, and this blood provides ZAP-70 positive NK and T-cells, as well as ZAP-70 negative normal B-cells. The normal blood thus controls for cell separation, as well as fixation, permeation and staining, while providing three levels of ZAP 70 expression.

EXAMPLE 6

Evaluation

Finally, based on the available data, it is apparent that a simple single cutoff system for presence or absence of ZAP-70 is too simplistic and does not accurately reflect the biology of CLL. Instead we propose a two cutoff system, providing three ranges ZAP-70 expression—positive, negative, and an in-between, indeterminate region where ZAP-70 expression is inconclusive. Under the conditions described herein, we have set the cutoff values at 2,100 MESF (30% positive), and 1,350 MESF (55% negative) with the intervening region being 15% indeterminate. Studies of patient samples show this grouping indicates our quantitative assay matches the published distribution of patients with known IgVH status.

TABLE 5

| Data |
|---|
| Normal Ranges: |
| B-cells: 300-900 median MESF<br>T-cells: 4300-9000 median MESF<br>Patient: |
| Negative ≦ 1350<br>Intermediate = 1,350-2,100<br>Positive ≧ 2100 |

*These ranges were determined in-house and may be subject to change due to ongoing evaluation.

Figure 7:
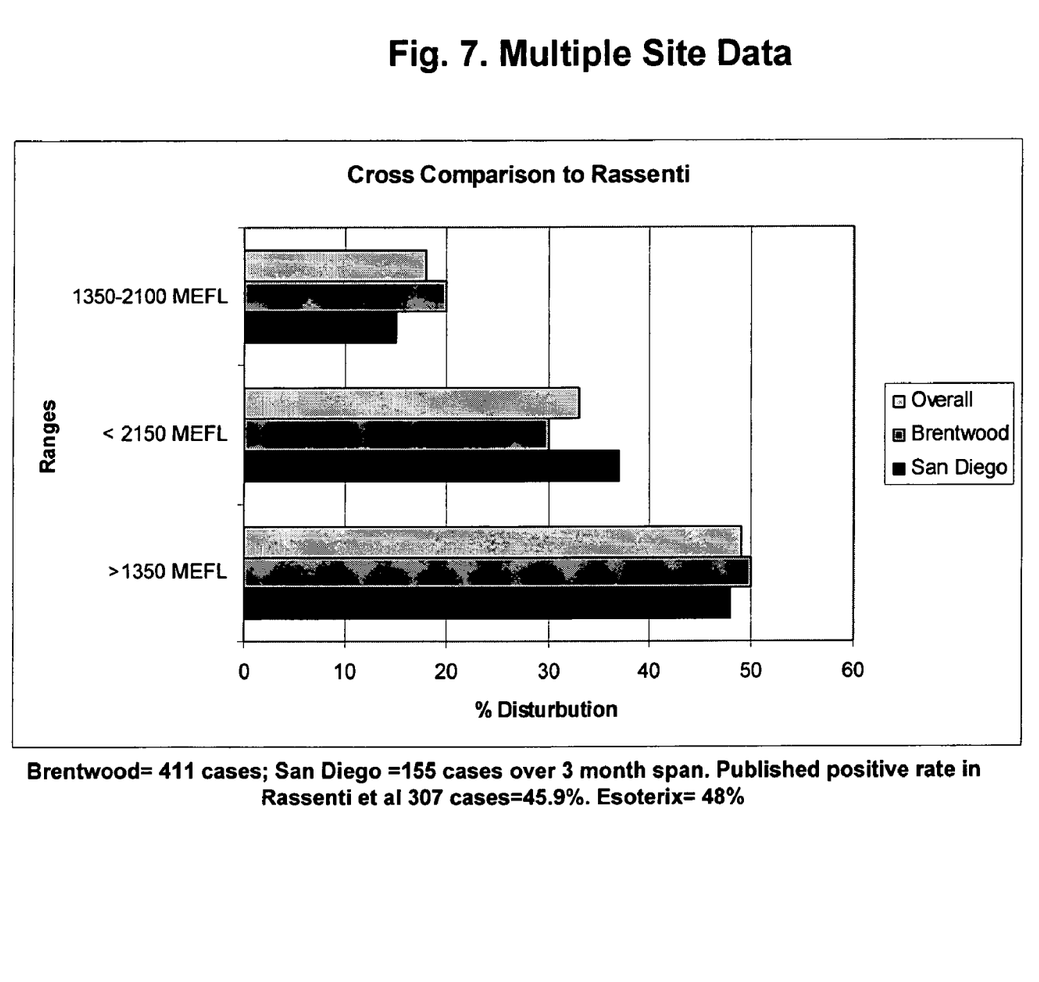
FIG. 7. Multiple Site data. Showing that the assay is reproducible across different laboratories.

Further the assay was repeated at two locations to determine whether is was reproducible across sites. The data in FIG. 7 shows that the assay is very reproducible.

The following articles are incorporated by reference in their entirety:

Admirand J. H. et al., Immunohistochemical detection of ZAP-70 in 341 cases of non-Hodgkin and Hodgkin lymphoma, Mod Pathol. 17(8):954-61 (2004)

Byrd J C, et al., Chronic lymphocytic leukemia, Hematology (Am Soc Hematol Educ Program) 1:163-83 (2004).

Crespo M., et al., ZAP-70 expression as a surrogate for immunoglobulin-variable-region mutations in chronic lymphocytic leukemia. N Engl J Med 348 (18): 1764-75 (2003).

Herishanu Y., et al., Quantitative flow cytometry of ZAP-70 levels in CLL using molecules of equivalent soluble fluorochrome: B-CLL cell and T-cell ZAP-70 levels correlate with disease progression, Leukemia & Lymphoma 46(S1): S50 (2005).

Letestu R., et al., Evaluation of ZAP-70 expression by flow cytometry in chronic lymphocytic leukemia: a multicentric international harmonization process, Leukemia & Lymphoma 46(S1): S47 (2005).

Orchard J A, et al., ZAP-70 expression and prognosis in chronic lymphocytic leukaemia. Lancet 363 (9403): 105-11 (2004).

Makoto Otsu, et al., Reconstitution of lymphoid development and function in ZAP-70-deficient mice following gene transfer into bone marrow cells, Blood, 100(4): 1248-1256 (2002).

Rassenti L Z, et al., ZAP-70 compared with immunoglobulin heavy-chain gene mutation status as a predictor of disease progression in chronic lymphocytic leukemia. N Engl J Med 351 (9): 893-901 (2004).

Rosenwald et al., Relation of Gene Expression Phenotype to Immunoglobulin Mutation Genotype in B-cell Chronic Lymphocytic Leukemia, The Journal of Experimental Medicine, 149:1639-1647 (2001).

Sakaguchi N, et al., Altered thymic T-cell selection due to a mutation of the ZAP-70 gene causes autoimmune arthritis in mice, Nature. 426(6965):454-60 (2003).

What is claimed is:

1. A quantitative ZAP-70 assay for predicting the prognosis of chronic lymphocytic leukemia (CLL), comprising the steps of:
   (a) staining a patient blood sample with an anti ZAP-70 antibody, an anti-T cell antibody and an anti-B-cell antibody;
   (b) measuring anti-ZAP-70 antibody staining in the B-cells and T-cells to obtain a mean fluorescent intensity (MFI) in each of the B-cells and the T-cells;
   (c) converting the median of the MFI to molecules of equivalent fluorochrome (MEFL), wherein an amount of ZAP-70 is reported as an MEFL value, and
   (d) determining (i) if the amount of ZAP-70 in the B-cells or the T-cells of the patient blood sample is in the top 30% of a preestablished range of patient MEFL values for at least one of the B-cells or T-cells so as to indicate that the patient has progressive CLL, or (ii) if the amount of ZAP-70 in the B-cells of the patient blood sample is in the lower 55% of a pre-established range for the at least one of the B-cells or T-cells so as to indicate that the patient has indolent CLL.

2. The method of claim 1, wherein the amount of ZAP-70 in the patient sample is compared to an amount of ZAP-70 as measured in a control cell population comprising a mixture of ZAP-70$^+$T-cells and ZAP-70$^-$B-cells.

3. The method of claim 2, wherein the control cell population is a mixture of Jurkat and Ramos cells.

4. The method of claim 2, wherein the amount of ZAP-70 in the control cell population is measured prior to measuring ZAP-70 in the patient sample, and wherein the ZAP-70 in patient blood sample is measured if the amount of ZAP-70 in the control cell population is within the pre-established range of ZAP-70 for normal and indolent CLL B-cells and T-cells.

5. The method of claim 2, wherein the B-cells and T-cells of the patient blood sample and the control cell population are electronically separated by flow cytometry.

6. The method of claim 1, further comprising repeating steps (a)-(d) using normal human blood rather than a patient blood sample and confirming that ZAP-70 in the normal human blood is within a pre-established range of ZAP-70 for B-cells and T-cells in normal blood.

7. The method of claim 1, wherein anti-T-cell antibody is anti-CD5 antibody, and the anti-B-cell antibody is anti-CD 19 antibody.

8. The method of claim 1, wherein the B-cells and T-cells of the patient blood sample are electronically separated by flow cytometry.

9. The method of claim 6, wherein the B-cells and T-cells of the patient blood sample and the normal blood sample are electronically separated by flow cytometry.

10. The method of claim 1, wherein a MEFL value of >2100 in the patient B-cells indicates the patient has progressive CLL, and a MEFL value of <1350 in the patient B-cells indicates the patient has indolent CLL.

11. A quantitative ZAP-70 assay, comprising the steps of: (a) staining (i) a first control cell population, (ii) a sample of normal human blood, and (iii) patient blood sample each comprising a mixture of T-cells and B-cells with an anti-ZAP-70 antibody, an anti-CD 19 antibody and an anti-CD5 antibody, wherein the mixture of B-cells and T-cells present in the control cell population is a mixture of Ramos and Jurkat cells; (b) for each of samples (i), (ii) and (iii), separating the B-cells and T-cells by flow cytometry using the anti-CD 19 antibody and the anti-CD5 antibody; (c) measuring in each of samples (i), (ii) and (iii) anti-ZAP-70 antibody as a mean fluorescent intensity (MFI) in the separated B-cells and T-cells; (d) converting each MFI for (i), (ii) and (iii) to molecules of equivalent fluorochrome (MEFL) using the median of the MFI to determine the amount of ZAP 70; and (e) providing a prognosis for the patient, wherein an amount of ZAP-70 in B-cells of the patient blood sample in the top 30% of the pre-established MEFL range for patient B-cells indicates that the patient has a shorter time to progression of chronic lymphocytic leukemia (CLL), and an amount of ZAP-70 in B-cells of the patient blood sample in the lower 55% of the pre-established MEFL range for patient B-cells indicates that the patient has indolent CLL.

12. The method of claim 11, wherein a MEFL value of >2100 in the patient B-cells indicates the patient has progressive CLL, and a MEFL value of <1350 the patient B-cells indicates the patient has indolent CLL.

* * * * *

UNITED STATES PATENT AND TRADEMARK OFFICE
CERTIFICATE OF CORRECTION

| | | |
|---|---|---|
| PATENT NO. | : 8,163,510 B2 | Page 1 of 1 |
| APPLICATION NO. | : 12/838906 | |
| DATED | : April 24, 2012 | |
| INVENTOR(S) | : Keith E. Shults et al. | |

It is certified that error appears in the above-identified patent and that said Letters Patent is hereby corrected as shown below:

Page 1, Column 1, Line 19, After "Oct. 14, 2005" insert -- , now Pat. No. 7,759,076 --.

Column 10, Line 62, delete "Negative $\leqq$ 1350", insert -- Negative $\leq$ 1350 --.

Column 10, Line 64, delete "Positive $\geqq$ 2100", insert -- Positive $\geq$ 2100 --.

Claim 12, Column 12, Line 58, delete "of >2100", insert -- of $\geq$ 2100 --.

Claim 12, Column 12, Line 59, delete "of <1350", insert -- of $\leq$ 1350 --.

Signed and Sealed this
Twenty-third Day of October, 2012

David J. Kappos
*Director of the United States Patent and Trademark Office*